United States Patent [19]
Halverson et al.

[11] Patent Number: 5,508,165
[45] Date of Patent: Apr. 16, 1996

[54] AVIAN SEX DETERMINATION PROBE

[75] Inventors: Joy L. Halverson; Jan Dvorak, both of Davis, Calif.

[73] Assignee: Zoogen, Inc., Davis, Calif.

[21] Appl. No.: 194,131

[22] Filed: Feb. 9, 1994

Related U.S. Application Data

[63] Continuation of Ser. No. 947,100, Sep. 17, 1992, abandoned, which is a continuation of Ser. No. 585,915, Sep. 21, 1990, abandoned.

[51] Int. Cl.$^6$ .................... C12Q 1/68; C07H 21/04
[52] U.S. Cl. .................... 435/6; 435/320.1; 436/94; 536/24.3; 536/24.31
[58] Field of Search .................... 435/6, 320.1, 810; 436/94; 536/24.3, 24.31

[56] References Cited

U.S. PATENT DOCUMENTS 5,215,884  6/1993  McGraw, III .................... 435/6

FOREIGN PATENT DOCUMENTS 63-258580  10/1988  Japan.
63-258581  10/1988  Japan.

OTHER PUBLICATIONS

Nichirei Dialog No. 88–348691/49 Japan Patent 63258580 (1988) (Abstract).
Nichirei Dialog No. 88–348692/49 Japan Patent 63258581 (1988) (Abstract).
Weeks et al, Proc Natl Acad Sci USA, vol. 84 (1987) 2798–2802.
Dvorak et al., *J. Hered.* 83(1), 22–25 (1992) (Abstract).

*Primary Examiner*—W. Gary Jones
*Assistant Examiner*—Kenneth R. Horlick
*Attorney, Agent, or Firm*—Bertram I. Rowland; Pamela J. Sherwood

[57] ABSTRACT

Avian cDNA nucleotide sequences for use as hybridization probes are provided. Probes derived from the sequences find use in defining the sex of a bird, usually by producing hybridization patterns that are sex-specific for most avian species. For a given avian species the probes may hybridize to both Z and W chromosomes so as to differentiate between the two chromosomes on the basis of restriction fragment length polymorphisms. Alternatively, the probes may hybridize exclusively to one of the two sex chromosomes in some species. The hybridization probes taught are also useful for the isolation of other nucleotide sequences that may be used to generate sex-specific hybridization patterns.

14 Claims, No Drawings

AVIAN SEX DETERMINATION PROBE

This is a continuation of application Ser. No. 07/947,100 filed Sep. 17, 1992, abandoned, which is a continuation of application Ser. No. 07/585,915 filed Sep. 21, 1990 abandoned.

TECHNICAL FIELD

This invention relates to the field of restriction fragment length polymorphism markers suitable for sex identification in avian species, and methods for using such markers.

BACKGROUND

RFLP (restriction fragment length polymorphism) analysis has proven highly successful in mapping and discovering new genes in eukaryotic organisms. RFLP marker probes consist of polynucleotide sequences that specifically hybridize to a region of the chromosome. These chromosomal regions of hybridization are revealed to be polymorphic between individuals of the same species when the chromosomal DNA is digested by restriction endonucleases and analyzed by hybridization analysis. Different RFLP alleles are distinguished from one another on the basis of the hybridization banding patterns produced after size separation. Genetic linkage analysis between RFLP markers and uncharacterized genes has proven to be a useful technique for isolating and mapping uncharacterized genes of interest. Although the RFLP marker has most frequently been used to identify the chromosomal disruptions responsible for genetic diseases, it is also of interest to use RFLP markers in deciphering other complex genetic regulatory questions, such as sexual development in animals.

While the genetics and biochemistry of sex determination in mammals has been the subject of extensive scientific investigation, similar studies have not been carried out with respect to birds. This is surprising in view of the commercial importance of numerous avian species e.g., chickens and turkeys. It is of interest to provide research tools useful for deciphering the complex process of genetic sex determination in birds. Sex-specific genetic markers are of particular interest. Such markers may be used to sexually identify immature birds prior to the development of gender specific morphological differences. Early sexual identification is an important consideration when breeding those birds that become sexually mature prior to the development of external sexual characteristics. Accordingly, there is interest in providing methods for preventing undesired matings by permitting gender identification (and gender separation) prior to the development of sexual maturity.

Genetic sexual identification is also useful in the breeding of rare bird species with unidentified secondary sexual characteristics; captive breeding programs may thus be effectively organized.

Sex chromosomes, as opposed to autosomal chromosomes, differ with respect to one another in size and genetic composition. Thus, some regions of one sex chromosome contains genes which have no corresponding allele on the other sex chromosome.

One of the principal ways in which the sex chromosomes of birds differ from man and other mammals is that the female bird is the "heterogametic" sex, having Z and W sex chromosomes. In mammals, the male is the "heterogametic" sex having both X and Y chromosomes whereas the female is "homogametic" having two X chromosomes.

It is of interest to provide RFLP genetic markers suitable for the identification of DNA regions which are diagnostic of the sex of the bird, where the DNA regions may be common to the Z and W chromosomes such that RFLP's unique to each sex chromosomes may be detected; or the DNA region is unique to one of the sex chromosomes, so that the amount or presence of the RFLP will determine the sex of the bird. Such genetic markers permit the identification of the chromosomally specified sex of an individual bird based on analysis of a DNA preparation derived from the bird.

Relevant Literature

Halverson J., Dvorak, J., Flammer, K. 1985. A new method of avian sex determination- identification of the W body by C-banding of erythrocytes. Proceedings of the Annual Meeting of the Association of Avian Veterinarians. 1985. Boulder, Colo.

Halverson, J., Rauen, K., 1988. The molecular approach to poultry breeding. Proceedings of the Thirty-seventh Western Poultry Disease Conference and Molecular Biology Workshop. 1988. Davis, Calif.

SUMMARY OF THE INVENTION

Avian nucleotide sequences for use as a source of hybridization probes are provided. Probes derived from these sequences, Tsex (also designated as pMg1) and related sequences, are used in hybridization for sex identification of many avian species. Procedures are given for using the probes so as to sexually identify individual birds. For a given avian species, the probes may hybridize to both Z and W chromosomes allowing for differentiation between the two chromosomes on the basis of restriction fragment length polymorphisms. Alternatively, the probes may hybridize exclusively to one of the two sex chromosomes in some species, thus permitting gender identification on the basis of sex-specific hybridization intensity. The probes provide a means for identifying the gender of a bird without reliance on morphological characteristics. The probes also find use in recovering and identifying nucleotide sequences homologous to Tsex and sex-specific nucleotide sequences that are genetically linked to genomic Tsex or Tsex-homologous sequences.

DESCRIPTION OF THE SPECIFIC EMBODIMENTS

Novel nucleic acid sequences and methods for using the sequences are provided for determining the chromosomally specified sex of individual birds. The method is based on the ability of hybridization probes derived from the nucleic acid sequences to hybridize with sequences from the sex chromosomes of birds being analyzed for sexual identification. The nucleic acid sequences provided for, namely Tsex, derivatives thereof, and equivalent sequences, are homologous to nucleic acid sequences present on both or one of the Z and W chromosomes of most birds tested. However, there do exist avian species in which Tsex-homologous sequences are only present on one of the two sex chromosomes. For bird DNA, the term homologous when applied to nucleic acid sequences intends nucleic acid sequences capable of hybridizing to each other at a stringency of at least about 25° C. below the $T_m$ ($T_m$ is the temperature at which about half the nucleic acid strands are denatured). In referring to "Tsex homologous sequences" it is intended to include the Tsex sequence itself. Most generally used hybridization protocols may be used with Tsex-derived probes. See *Molecular Cloning: A Laboratory Manual*, second edition (1989), Sambrook et al., Cold Spring Harbor Laboratories Press, Cold Spring Harbor, N.Y., for examples of such protocols.

The subject invention permits the identification of the chromosomally specified sex of a given bird based on a hybridization analysis of genomic DNA extracted from the individual bird being gender tested. Suitable birds for chromosomal identification by Tsex hybridization have Tsex-homologous sequences present on one or both sex chromosomes.

The subject invention provides a means for identifying the gender of avian species without relying on morphological sexual characteristics. Thus the subject invention may be used to identify the sex of birds when secondary (external) sexual characteristics are absent or unknown. The identification of sex in the absence of secondary sexual characteristics is useful because in commercial breeding operations it is advantageous to separate sexually mature birds from one another in order to prevent undesired matings. This separation may be difficult to achieve because some avian species become sexually mature prior to the development of obvious external sexual differences. Thus, by providing for a simple and reliable means of gender identification prior to the development of external sexual characteristics in birds, the subject invention finds use in commercial bird breeding. The subject invention finds use in determining the gender of rare bird species in which the gender specific external characteristics are unknown. By permitting the creation of breeding pairs, the subject invention provides a rational means of breeding rare birds.

Hybridization probes derived from Tsex find a variety of uses in addition to their use in sexual identification. Tsex-derived hybridization probes may be used to isolate Tsex-homologous sequences. Such isolation may be achieved by screening recombinant DNA libraries prepared from avian DNA (or cDNA) from species other than turkey (the Tsex sequence being derived from a turkey cDNA). In addition, these Tsex probes may be used to isolate full length cDNAs for Tsex and the Tsex genomic sequences. Similarly, Tsex-derived hybridization probes may also be used in chromosome walking or jumping techniques to isolate coding and non-coding sequences chromosomally proximal, though not necessarily adjoining, to Tsex-homologous sequences. Tsex sequence derived probes may be employed with chromosome walking and jumping techniques as described in a number of commonly available publications, e.g., Sambrook et al., supra.

Additional uses of the subject invention are found in the isolation of sex determination mutations in avian species. Mutations affecting sex determination have found use in manipulating progeny phenotype in the controlled breeding of numerous animals (e.g., linked X chromosomes, autosomal-sex chromosome translocations). The subject invention facilitates the discovery of sex determination mutants by allowing investigators to determine the sexually specified genotype of mutant birds with questionable sexual morphology.

The Tsex sequence was obtained from a cDNA library prepared from turkey embryonic poly(A)mRNA. The Tsex sequence is 959 base pairs in length. The sequence of Tsex is displayed in Table 1.

TABLE 1

| Sequence of Tsex |
| --- |
| 1   5'AACAGCATCT GATGCTGCAC CCCTTCAGTA TCTGGCTCCC TACTCAGGCT |
| 51  GCTCCATGGG GGAATACTTC AGAGACAATG GGAAACATGC ATTGATCATC |
| 101 TACGATGACT TGTCCAAACA GGCTGTTGCC TACCGTCAGA TGTCTCTGCT |
| 151 GCTGCGTCGT CCGCCTGGCC GTGAAGCTTA CCCAGGTGAT GTGTTGTACC |
| 201 TGCACTCTCG CCTGCTGGAG AGAGCAGCTA AAATGAATGA TTCCTTTGGA |
| 251 GGAGGCTCTC TGACTGCTTT GCCCGTCATT GAAACTCAGG CTGGTGATGT |
| 301 GTCTGCTTAC ATTCCAACCA ATGTCATCTC CATCACTGAT GGACAGATCT |
| 351 TCTTGGAAAC TGAACTGTTC TACAAAGGTA TCCGTCCAGC CATCAACGTT |
| 401 GGTCTGTCTG TGTCCCGTGT GGGTTCTGCT GCTCAGACCA GGGCAATGAA |
| 451 ACAGGTGGCT GGTACCATGA AGCTGGAGCT GGCTCAGTAC CGTGAAGTGG |
| 501 CTGCCTTTGC TCAGTTTGGG TCTGATTTGG ATGCTGCCAC ACAACAGCTG |
| 551 CTGAATCGTG GTGTGCGTCT GACAGAGCTC CTGAAACAAG GACAGTATGT |
| 601 TCCCATGGCT ATTGAGGAAC AGGTTGCAGT CATCTATCGT GGTGTAAGAG |
| 651 GTCACTTGGA CAAGCTGGAG CCCAGCAAAA TCACTAAATT TGAGAGTGCT |
| 701 TTCCTGGCTC ATGTACTGAG CCAGGACCAG GCCCTCCCTC TCCACCATCA |
| 751 GGACTGAAGG GAAGATCTCT GACCAGACGG AAGCTAAGCT GAAGGAAATA |
| 801 GTCACAAATT TCCTATCTAC TTTTGAGGCA TAAACTCATT ATCTGTTCAA |
| 851 ACAGACCAGG CTGTTTTTGT TGTTACGTGC TTTGCCTCCA TCAAAGACCT |
| 901 AAACGTATCG AGTGCTTGAA TGTACAGATC TCACTGAGAA TAAAAGTTTC CATGTAAAA3' |

Sequence displayed from position 1 to end (position 959)

The Tsex sequence may be used for the production of a variety of nucleic acid hybridization probes, also referred to as Tsex-derived probes. Hybridization probes based on the Tsex sequence find use for many purposes, including sex identification in birds and the isolation of Tsex-homologous sequences from a genetic library. Probes may be either single or double stranded, either RNA or DNA. Probes may be produced by in vitro or in vivo synthesis. Probes may also be produced by a combination of in vitro and in vivo synthesis. Methods of in vitro probe synthesis include organic chemical synthesis processes or enzymatically mediated synthesis, e.g., by means of SP6 RNA polymerase and a plasmid containing the Tsex sequence under the transcriptional control of an SP6 specific promoter. Usually, probes will have a specific complementary sequence of at least 12 nucleotides, more usually at least 14 nucleotides and preferably greater than 50 nucleotides and, more preferably having the entire Tsex sequence.

Probes may bear either complete or partial homology to Tsex. Probes containing partial homology to Tsex will usually have less than 20% mismatch with Tsex, and preferably less than 10% mismatch with Tsex.

When performing sex determination analysis using Tsex sequence derived probes not actually containing the complete 959 base pair Tsex sequence, the probes are preferably hybridized against DNA preparations from birds of known sex in order to verify that the probes produce the desired sex-specific hybridization pattern. Similarly, when sexing previously untested species of birds with Tsex sequence derived probes, the sex-specific nature of the hybridization patterns produced with Tsex sequence derived probes are preferably verified by hybridization against birds of known sex.

Probes may be modified by conjugation to a variety of labels which allow for detection of duplex formation between the probe and its complementary target. Labels include radioactive isotopes, ligands, e.g., biotin, enzymes, fluorescers and the like. A wide variety of protocols for labeling probes and detecting duplexes formed between probes and their target hybridization sequences have been described in the literature. See for example, Berger and Kimmel, editors, *Guide to Molecular Cloning Techniques* (1987) Academic Press Inc., San Diego, Calif.

Probe sequences may be joined to a variety of other nucleic acid sequences. Among these other nucleic acid sequences are vectors such as plasmids, cosmids, phages, and the like. By joining the probe sequence to a vector sequence, probes may be conveniently created, expanded, stored, and modified.

Nucleic acid preparations suitable for hybridization analysis with Tsex-derived probes may be isolated from any portion of a bird's body containing substantially intact nucleic acids. Preferably, nucleic acid preparation sources may be obtained without killing or injuring the bird and may be easily removed from the test bird. Preferred sources of starting material will be feather pulp, blood, or the like.

Tsex-derived hybridization probes may be used to determine the sex of an individual bird based on nucleic acid hybridization analysis. As previously discussed, hybridization analysis demonstrates that Tsex-homologous sequences are present on at least one, and usually both sex chromosomes of numerous avian species. For those species that have Tsex-homologous sequences present on both Z and W sex chromosomes, hereinafter called Tsex-double species, Tsex sequence derived hybridization probes may be used to distinguish male from female DNA preparations on the basis of the presence of at least one additional hybridization band present in the female chromosomal preparations. For those bird species having Tsex-homologous sequences present on only one sex chromosome, hereinafter called Tsex-single species, the genetically specified sex of the bird from which the DNA was prepared may be determined by employing a Tsex-specific probe and semiquantitatively comparing the degree of hybridization of the probe to a sample with the degree of hybridization of the same probe to a standard of known sex.

Tsex-double species include, but are not limited to: turkeys, chickens, Canada geese, pheasants, zebra finches, lapwings, sandgrouse, murres, caiques (including: white-bellied and black-headed), macaws (including: blue & gold, scarlet, hyacinth, yellow-collar, hahns, greenwing, and military), red-bellied parrots, amazons (including: Mexican red-headed, orangewing, red lored, mitred, cherry-head, yellow-nape, and blue-front), cockatoos (including: rose-breasted, goffins, umbrella, mollucan, and sulfur-crest), lorries, cockatiels, budgerigars, and rosellas.

Tsex-single bird species include but are not limited to: African grey parrots, Eclectus parrots, Lovebird, and Conures (including: Halfmoon, Patagonian, and Nanday).

Some bird species are not amenable to sex identification with Tsex-derived probes with the restriction endonucleases employed, but may be capable of identification with an appropriate endonuclease. Tsex-derived probes hybridize to sequences on both the W and the Z chromosomes in these species; however, the hybridization patterns produced do not vary between the sexes. The only species tested that are not currently amenable to sex identification with Tsex-derived probes are bald eagles, red tail hawks, ostriches, penguins, cinerous vultures, and Russell Griffon vultures.

The preferred method of sex identification by hybridization analysis with Tsex-derived nucleic acid hybridization probes requires the immobilization of target hybridization sequences onto a solid support. Avian sex identification employing the process of nucleic acid hybridization with Tsex-specific probes may utilize solid immobilization supports suitable for hybridization analysis with most generally recognized nucleic acid hybridization procedures. Suitable support membranes capable of binding nucleic acids include nitrocellulose, Nytran™, Zetaprobe™ and the like. A variety of protocols for immobilizing nucleic acids to membranes have been described in the literature. See for example, Berger and Kimmel, supra. The immobilization procedure may be mediated by capillary transfer, electrophoretic transfer, vacuum transfer and the like. The amount of nucleic acid transferred to the solid support membrane will generally be in the range of about 0.01 μg to 20 μg, preferably in the range of about 0.05–5 μg, per sample for analysis.

Chromosomal DNA preparations suitable for hybridization with Tsex-derived probes may be digested with restriction endonucleases prior to the transfer of the nucleic acids to an immobilizing support, usually after size separation where the sex is determined based on the difference in size of one or more fragments. Prior to immobilization, chromosomal DNA preparations from Tsex-double species must be digested with at least one restriction endonuclease, whereas chromosomal DNA from Tsex-single species are preferably, though not essentially, digested with at least one restriction endonuclease. Useful restriction endonuclease are selected for their ability to produce a sex-specific hybridization pattern when hybridized against Tsex-derived probes. Where restriction sites are present in the Tsex- or homologous DNA, a number of fragments which bind to the probe may be produced. Digestion with suitable restriction endonucleases produces chromosomal fragments with sizes capable of being separated by electrophoresis.

When DNA preparations for gender determination analysis are subjected to restriction endonuclease digestion, the DNA preparations are size separated by electrophoresis, and transferred in situ from the gel electrophoresis separation medium to a nucleic acid binding support. Electrophoretic separation should proceed to a point where the degree of chromosome digest fragment separation achieved by electrophoresis is sufficient to separate Tsex-homologous chromosomal fragments from one another to an extent capable of being detected by hybridization analysis. Suitable gel electrophoresis separation media include agarose, polyacrylamide, mixtures thereof, and the like, at a concentration suitable for the separation of nucleic acid fragments to an extent sufficient to reveal size differences between Tsex-homologous DNA fragments. The in situ transfer of nucleic acids to a binding membrane may be achieved by any of the standard procedures for hybridization analysis. Exemplary, but not exclusive of such procedures are Southern blotting and electroblotting.

After immobilization to a solid support, the samples are hybridized against Tsex-derived hybridization probes.

Duplexes formed between the labeled probe and the Tsex-homologous sequences in the samples for analysis and any hybridization standards present are subsequently visualized by methods appropriate to the probe label.

When performing chromosomal sex analysis on Tsex-double species, male and female chromosomal DNA hybridization sex standards are optionally, although preferably, present. By hybridization standards, it is intended chromosomal DNA from an individual of known sex and of the same species as the individual undergoing sex determination analysis; the standard is also present in a quantity essentially the same as the DNA sample for analysis.

Male and female DNA samples from Tsex-double species may be distinguished from one another by the presence of at least one hybridization band found in the chromosomal preparation of one sex that is not found in preparations of the other sex. Since, frequently one obtains a plurality of bands of different sizes which bind to the probe, all that is required to distinguish the sex of the subject bird is that there be a band of a size characteristic of a particular sex, where the absence of the band is characteristic of the other sex. Furthermore, the intensity of the hybridization bands in common between male and female chromosomal DNA preparations have greater (usually approximately double) hybridization intensity in male derived samples because of the double dose of target DNA from the two Z chromosomes. Thus, by comparing DNA samples for analysis with each other, or comparing the samples with known male and female standards of the same species, the sex of the individual animal providing the DNA for analysis may be determined.

Sex identification in Tsex-single species is performed essentially the same as in Tsex-double species; however, the restriction endonuclease digestion and electrophoresis separation steps are optional (although preferably performed) rather than required as with the analysis of Tsex-double species. When analyzing Tsex-single species, all DNA samples for analysis and hybridization standards are necessarily present in approximately the same quantity so that the intensity of hybridization produced may be accurately compared among samples and hybridization standards.

In Tsex-single species where Tsex-homologous sequences are only present on the Z chromosome, probe hybridization with chromosomal preparations from males displays greater (approximately double) hybridization intensity than probe hybridization with equal quantities of DNA from female members of the same species.

Tsex-derived probes also find use in isolating other sex-specific sequences. As previously discussed, Tsex-derived probes are useful for sex identification because hybridization with these probes reveals sexspecific hybridization patterns. Since the Tsex probes which hybridize to the W and Z chromosomes are the same sequence, it is apparent that the sex-specific nature of the hybridization must be attributable to chromosomal sequences other than Tsex itself (or Tsex-homologous sequences in species other than turkey). Thus on the chromosome, Tsex-homologous sequences lie close to nucleic acid sequences that differ from one another in a sex-specific manner. These as yet unidentified sex-specific sequences may be detected by employing conventional library screening techniques, including chromosome walking (Bender et al., *J. Mol. Biol.* (1983) 168:17) and chromosome Jumping (Poustka et al. *Nature* (1987) 325:323), to recover sequences proximal to Tsex-homologous sequences, in which at least the first round of library screening employs a Tsex sequence derived probe. These library screening techniques are discussed at length in Berger and Kimmel, supra and Sambrook et al., supra.

Genetic libraries for screening with Tsex-derived probes may be prepared in plasmid, cosmid, or YAC (yeast artificial chromosome) vectors or the like. Portions of nucleotide sequences isolated in a first round of screening that are not homologous to Tsex may be labeled and used as probes for a second round of library screening. The process of repeatedly screening a library with newly isolated sequences may be repeated as desired so as to "walk" or "jump" down the chromosome. Progression down the chromosome from the Tsex homologous region may proceed in either direction. The region of the chromosome analyzed by "walking" techniques and the like may extend for a distance greater than 5000 kb to either side of the Tsex region (or Tsex-homologous region), however preferred distances for walking are in the range of about 100–1000 kb. Chromosomal regions of interest also include introns within the Tsex-homologous genomic sequence. Nucleotide sequences not homologous to Tsex that are isolated during "walking" may be screened for their ability to produce sex-specific hybridization patterns when used as hybridization probes. It is also of interest to engage in chromosome walking for the purpose of isolating sex-specific nucleotide sequences in those bird species that have non-polymorphic Tsex-homologous sequences on both the W and the Z chromosomes, e.g., penguins.

For an example of using Tsex to isolate additional sex-specific nucleotide sequences, consider the case of screening a turkey genomic library with a labeled Tsex DNA sequence as a probe. Plasmids from individual clones recovered in the screening may then be restriction mapped and regions of the recovered plasmids not homologous to Tsex isolated. The isolated regions may then be labeled for use as probes in a second round of library screening. Sequences recovered from library screening may also be tested for use as sex-specific probes by labeling the newly isolated sequences and hybridizing the labeled sequences against Southern blots containing restriction digested genomic DNA from both male and female birds (of the same species). Sequences that reveal sex-specific hybridization pattern polymorphisms may find use in sex identification protocols similar to those employing Tsex-derived probes.

Besides using the nucleic acid as an identifier of sex, the expression product may also be used to identify sex. To the extent that the expression products of the two sequences differ as to epitopes, antisera or monoclonal antibodies may be prepared which will distinguish between the two alleles, when the Tsex or related gene is present on both chromosomes. Where the gene is only on one chromosome, the amount or presence of the protein will indicate the sex of the bird. Various immunoassays may be used to detect the proteins, using radioisotopes, enzymes, chromophores, fluorophores, chemiluminescers, or the like, as detectable labels.

Kits may be provided with probes and standards for determining the sex of birds. Thus, by carrying out the assay with the sample and having genomic DNA which may be processed in the same manner, the results may be compared directly. Thus, the kit would comprise, one or more probes, usually one probe, generally labeled, and genomic DNA for one or both sexes of the bird of interest for processing in the assay and comparison with the sample DNA.

The invention now being generally described, the same will be better understood by reference to the following examples which are provided for purposes of illustration only and are not to be considered limiting of the invention unless so specified.

EXAMPLES

RNA Isolation

A cDNA library was prepared from poly A mRNA isolated from turkey embryos. All RNA isolation procedures and manipulations were performed in RNAse free laboratory articles. In order to remove RNAse contamination, glassware was baked at 180° to 190° C. overnight and plasticware was treated with a 0.2% diethylpyrocarbonate (DEPC) solution.

8.3 gms of 3, 4, and 5 day old turkey embryos were pooled together and placed in a lysis buffer (7 ml of buffer/1 gm tissue). The lysis buffer is composed of:

4M Guanidinium isothiocyanate
0.2M Tris pH 7.5
0.01M EDTA
5% β mercaptoethanol (w/v)

The tissue was homogenized in a Polytron™ homogenizer at setting "5" for 1 minute. The homogenate was strained through a cheese cloth and a myra cloth filter (a double layer in which the homogenate first passes through the cheese cloth). The filtrate was then centrifuged at 10,000×g at 25° C. for 10 minutes. The supernatant was removed and N lauryl sarcosine was added until a final concentration of 0.5% was reached. Seven volumes of 4M LiCl were then added. The supernatant was then allowed to sit for 15–20 hours at 4° C. The solution was then centrifuged at 10,000×g for 90 minutes at 4° C. The supernatant was removed, and the pellet was resuspended in 100 ml of 3M LiCl. The solution containing the resuspended pellet was then centrifuged at 10,000×g for 60 minutes at 4° C. and the supernatant removed. The pellet was then dissolved in a solubilization buffer by vortexing. RNA solubilization buffer: 0.1% SDS, 0.01M pH 7.5 Tris, EDTA pH 8 0.5 mM (about 50 ml buffer/10 gm sample). The RNA was then extracted with an equal volume of phenol:chloroform:isoamyl alcohol (25:25:1) solution. The aqueous phase of the extraction was saved and a 3M potassium acetate solution was added to make a solution with a final concentration of 0.2 molar potassium acetate. 2.2 volumes of 95% ethanol were then added. The solution was dispensed into 30 ml Corex™ tubes. The Corex™ tubes were stored at −20° C. overnight. The tubes were then centrifuged at 10,000×g for 30 minutes at 4° C. The supernatant was removed and the pellet was washed with a 70% ethanol solution. The tube was allowed to drain and then subsequently dried in a vacuum oven for 20–60 minutes. The pellet was then resuspended in sterile deionized water.

Isolation of Poly A mRNA

Poly A mRNA isolated from the total embryonic turkey RNA preparation by oligo(dT)-cellulose was equilibrated with about 2 ml of loading buffer (loading buffer; 20 mM Tris pH 7.5, 0.1 mM EDTA, 0.5M LiCl, 0.1% SDS). The oligo (dT)-cellulose slurry was poured into a 1.0 ml siliconized Pasteur pipette (plugged with siliconized glass-wool). The column was washed with 3 volumes each of (1) sterile deionized water, (2) 0.1M NaOH, 5 mM EDTA, (3) sterile deionized water. The column was washed with water until the column effluent had a pH of less than 8.0. The column was then washed with 5 volumes of loading buffer. An aqueous solution containing the total RNA isolated from turkey embryos was heated to 65° C. for 5 minutes. Equal volumes of 2× loading buffer was added to the RNA solution and the solution was allowed to cool to room temperature. The solution was then applied to the top of the oligo(dT)-cellulose column. The column effluent was collected and heated again to 65° C. and reapplied to the top of the column. The column was then washed with 5 mls of loading buffer. 1 ml aliquots of column effluent were collected. 5 volumes of 0.1M LiCl buffer (20 mM Tris pH 7.5, 1 mM EDTA, 0.1M LiCl, 0.1% SDS) were then added to the column. The mRNA fraction was then eluted with 5 volumes of eluting buffer (1 mM Tris pH 7.5 1 mM EDTA, 0.05% SDS). 1.0 ml aliquots of column effluent were collected. The column was then rinsed with the deionized water, until the concentration of RNA in the effluent was approximately 0. The $A_{260}$ of each column fraction was determined in order to measure RNA concentration. The fractions were then stored at −70° C. in 70% ethanol and 0.2M potassium acetate.

cDNA Cloning

The embryonic turkey cDNA library was generated using the methods and vectors described by Alexander et al. "Dimer—Primer cDNA Cloning", *Methods in Enzymology* 154, Academic Press (1987). The cDNA was cloned into the SstI, site of pARC 7. Plasmid pARC 7 was digested with SstI and poly (dT) tailed using terminal deoxynucleotidyl transferase. Isolated embryonic turkey mRNA was allowed to anneal to the poly-dT tails via the poly-A tails of the mRNAs. After annealing to the poly-dT tail primers, the first strand of cDNA synthesis was catalyzed using murine Moloney leukemia virus reverse transcriptase. The first DNA strand was then poly-dG tailed using terminal deoxynucleotidyl transferase. The modified vector bearing cDNA strands on both termini was then digested with the restriction enzyme BamHI. A BamHI linker with a poly-dC tail was then annealed to the poly-dG tail at 42° C. The mixture was then cooled, permitting the constructs to circularize through the annealing of the BamHI sticky ends. Circularization was completed by the use of T4 DNA ligase. The RNA strand still remaining in the construction was removed by mixing the RNA-DNA duplex with RNase H and replacing the RNA with DNA using DNA polymerase I. The remaining nick was then closed with T4 DNA ligase and the constructs were transformed into *E. coli* strain DH5α.

Isolation of pTsex

Clones from the turkey embryonic cDNA library were selected at random and the plasmids within them prepared by a plasmid miniprep procedure (Birnboim and Doly, *Nucleic Acids Research* (1979) 7:1513). The turkey embryonic cDNA library plasmids were then screened by digestion with either PstI or XbaI, resulting in the release of the insert portion of the plasmid, and subsequent separation of the vector from the insert by agarose gel electrophoresis. Clones bearing inserts of greater than about 400 base pairs were subjected to further screening.

Further screening was carried out by radioactively labeling the cDNA portion of the isolated clones and using the resulting radioactive probe to screen Southern blots containing restriction digested chromosomal adult turkey DNA from both male and female turkeys. Prior to radioactive labeling, the inserts from the clones for further analysis were subjected to digestion with either PstI or XbaI, followed by separation of the digestion fragments from one another by agarose gel electrophoresis. The plasmid insert was isolated from the gel by electroelution. The insert was then radioactively labeled by nick translation. Nick translation was performed by placing the following mixture in a 1.5 ml eppendorf tube: 0.5 µg of insert DNA, 2.5 µl of 10× nick translation buffer (500 mM Tris pH 7.8, 50 mM MgCl, 100 mM β mercaptoethanol, 100 µg/ml BSA), 2.5 µl 2 mM dGTP, 2.5 µl 2 mM dTTP, 2.5 mM 2.0 mM dCTP, 5 µl dATP 3000 curies/mM $^{32}P$, 2 µl DNAse I (1 U/100 µl), 1 U DNA polymerase I, $H_2O$ to 25 µl total volume. The mixture was incubated 75 minutes at 15° C. 8 µl 0.25M EDTA was added, and the mixture was incubated 65° C. for 10 minutes to stop the reaction. 1 μl of 10 mg/ml sonicated salmon sperm DNA was then added in order to increase recovery of the probe. The unincorporated nucleotides were removed by gel filtration through a G-75 Sephadex column.

The $^{32}$P labeled inserts were then used as probes to hybridize with a Southern blot containing restriction digested chromosomal DNA prepared from turkey blood. Southern blots used for the screening of the embryonic turkey cDNA library contained chromosomal DNA from eight turkeys, four males and four females. 5 μg specimens of chromosomal DNA isolated from the blood of three male and three female turkeys were separately digested with BamHI and EcoR I. Also a single pair of chromosomal DNA preparations from male and female turkeys was digested with HindIII. The chromosomal digest fragments were separated by agarose gel electrophoresis and transferred to a Zetaprobe (BioRad) filter membrane by Southern blotting. All potential gender identification markers were tested against Southern blots containing this combination of restriction digested turkey chromosomal DNA.

The pre-hybridization solution (see section on hybridization conditions for the composition of this solution) was added to a polyethylene baggy containing the Southern blot and allowed to incubate at 65° C. overnight. The pre-hybridization solution was removed, and hybridization solution added. The hybridization solution was essentially the same as the pre-hybridization solution with the exception that the hybridization solution contained all of the probe labeled in the nick translation reaction (denatured at 95° C. for 10 minutes). The hybridization was allowed to proceed for 36 hours at 65° C.

After hybridization, the membranes were washed by the following procedure. The first wash was in a solution consisting of 1×SSC, 1% SDS, at 45° C. for 10–15 minutes. The blot was then washed in a solution of 0.1×SCC, 1% SDS, 0.1% sodium pyrophosphate, at 65° C. for 40 minutes. After washing, the blot was blotted dry on Whatman™ 3 MM paper, wrapped in saran wrap, and exposed to Kodak™ XAR X-ray film for three days. The X-ray film was subsequently analyzed for differences in the banding pattern between male and female chromosomal DNA preparations digested with the same restriction enzyme. The desired sex-specific probes should produce no variation in the banding patterns between DNA samples from members of the same sex.

The third embryonic turkey cDNA library clone tested by the above described procedure revealed a sex-specific hybridization pattern. Hybridization with this probe, named the Tsex sequence, with all three male turkey chromosomal DNA preparations digested with BamHI has revealed identical hybridization bands of 19.5 kb and 11.5 kb, whereas hybridization of pTsex with all three BamHI digested chromosomal DNA preparations from female turkeys resulted in the formation of hybridization bands with sizes of 19.5 kb, 13.5 kb, 11.5 kb, 7.3 kb, 6.4 kb and 5.5 kb.

EcoRI digested male chromosomal DNA probed with Tsex resulted in the formation of hybridization bands with sizes of about 13.5 kb, 3.9 kb and 3.4 kb whereas hybridization with EcoRI digested female turkey DNA resulted in the formation of hybridization bands with weights of about 13.5 kb, 9.1 kb, 3.9 kb, 3.4 kb and 2.3 kb. There was no variation in the hybridization patterns produced among the female DNA samples as well as among the male DNA samples.

Male chromosomal DNA digested with HindIII produced hybridization bands with weights of about 6.5 kb and 2.5 kb, whereas hybridization of chromosomal DNA resulted in the formation of hybridization bands with weights of about 6.5 kb, 5.7 kb, 5.3 kb, 4.4 kb, and 2.5 kb.

Blood Collection

Venous blood is collected by clipping a toenail sufficiently short that the blood vessel in the toenail (which usually ends in the distal quarter of the nail) is opened. After the blood has begun to ooze rapidly, a 20 μl Unopette™ pipette is held to the nail and blood is allowed to flow into the pipette quickly by capillary action. The other end of the Unopette™ fits onto the nozzle of a squirt bottle containing 70% ethanol. The ethanol is squirted through the pipette, washing the collected blood into a 2 ml polypropylene screw cap tube which is then capped. There should be no more than a 30 second delay between blood collection and mixing of the blood with 70% ethanol. The blood is now preserved and will be useful for DNA isolation during several weeks of storage at room temperature.

Blood can also be collected by venipuncture if desired. The wing vein (brachial vein) and jugular vein are preferred. The Unopette™ pipette can be used to transfer 20 μl of blood into the 2 ml tube for preservation in ethanol as described above. If blood is to be held for any time prior to preservation, it should be immediately chilled in an ice water bath and then held on ice.

Feather Pulp

The proximal shaft of primary feathers that are partially grown contain a mucinous pulp rich in DNA. Feathers are best removed by a firm, steady pulling motion which insures that the feather is removed intact, without leaving a stump. The proximal 2 inches of the feather is cut, and placed in 5 ml of a pre-chilled solution of DNA Isolation Buffer (DIB—0.1M NaCl, 0.1 mM EDTA, 10 mM Tris pH 7.0). The sample in buffer should be kept on ice until it can be used for DNA preparation.

GENOMIC DNA ISOLATION

Blood

The preserved blood, which appears as very fine, reddish-brown particles, is pelleted in a microfuge tube. The ethanol is decanted and the pellet resuspended in 1 ml of cold DIB by vortexing. The blood particles are again pelleted, the liquid decanted, and the pellet resuspended in 1 ml of cold DIB. After vortexing, the solution is poured into a 15 ml polypropylene screw cap tube. The microfuge tube is then rinsed with 1 ml cold DIB, and the wash is pooled with the previous extract. 2.5 ml of cold DIB containing 0.4 mg/ml proteinase K is then added to the 15 ml tube, and the tube placed in a 60° C. water-bath for 1–5 minutes. After warming the tubes, 0.5 ml 5% SDS (sodium lauryl sulfate) is added, and the tubes are capped and mixed by gentle inversion. The proteinase K digestion proceeds for 2–4 hours at 60° C. The proteinase K treated preparation is then phenol extracted as specified below.

Feather Pulp

The feather pulp is removed from the feather shaft by cutting along the length of the shaft with a fine scissors, splitting the shaft open, and teasing the pulp free. The pulp is placed in a chilled mortar with approximately ½ ml of quartz sand and covered with liquid nitrogen. After the pulp is frozen and the liquid nitrogen has evaporated, the material is ground with a pestle into a powder. The powder is mixed with 2 ml DIB and poured into a 15 ml polypropylene tube. The mortar is then rinsed with another 2 ml DIB which is subsequently combined with the first extract. 0.5 ml proteinase K (2 mg/ml) is then added and the tube placed at 60° C. for 1–5 minutes. After warming, 0.5 ml of 5% SDS is added, the tubes are capped, and then mixed by gentle inverting. The proteinase K digestion proceeds for 2–4 hours at 60° C. The proteinase K treated preparation is then phenol extracted as indicated below.

Phenol Extraction

After proteinase K digestion, 5 ml of Tris equilibrated phenol (pH 8.0) is added to the sample. (Phenol is equilibrated with Tris by the following procedure. Equal volumes pure phenol and 1M Tris-HCl, pH 8.0 are thoroughly mixed and allowed to separate. The Tris layer is removed and replaced with 0.1M Tris-HCl; pH 8.0 and the procedure repeated until the pH of the Tris layer is 8.0. Usually 2 or 3 changes of 0.1M Tris is required. The addition of 2 ml of 5M potassium hydroxide to the pure phenol decreases the number of extractions required.) After the addition of phenol, the samples are capped, wrapped in aluminum foil to prevent degradation of the phenol by exposure to light, and mixed thoroughly on a rocking shaker for 2–3 hours.

After shaking, the samples are incubated at 60° C. for 30 minutes in order to enhance separation of the aqueous layer, which contains phenol and denatured protein. These layers can be separated by a number of procedures: pipetting off the aqueous layer into a fresh tube, vacuum aspiration of the phenol layer, etc. A convenient method for handling large numbers of samples is to use silicon impregnated filter paper. A cone is formed from the paper and placed in a funnel. The entire sample (now at 60° C.) is poured into the cone. The paper retains the aqueous layer but allows the phenol layer to pass through. The contents of the cone are then poured back into the tube. Chloroform is then added to the sample to remove residual phenol. The sample is again gently mixed and then maintained at 4° C. for at least 2 hours. The sample is then poured into another separatory filter cone, which retains the aqueous layer but allows the chloroform to pass through. The content of the cone is then poured back into the tube.

The sample is adjusted to 0.3M sodium acetate (NaAc) by the addition of one-tenth volume of 3M sodium acetate. Two volumes of 95% ethanol are added and gently mixed with the sample. This procedure results in the extraction of water from the DNA, causing the DNA to precipitate into a white, stringy substance that can be physically picked up on a glass hook. The ethanol is poured off and the DNA on the hook is rinsed in approximately 2 ml of fresh 70% ethanol. The hook is then inverted so that the end with the DNA protrudes from the tube. The DNA sample is then allowed to air dry for several hours. The DNA is then resuspended in 400 μl of sterile TE (10 mM Tris HCl, 2 mM EDTA pH 8.0) in 2 ml polypropylene tubes with screw caps. The samples are placed on a rocking platform shaker and permitted to dissolve. The dissolving process usually requires several days at room temperature or 24 hours at 60° C.

Generally, 20 μl of blood yields 80–120 μg of DNA resulting in concentrations of 0.2–0.3 μg/μl. Quantitation is required with feather pulp samples due to sample variability and RNA (ribonucleic acid) contamination. Quantitation is also necessary when DNA is isolated from greater volumes of blood for research purposes.

| HYBRIDIZATION CONDITIONS 2X Prehybridization and 2X Hybridization Solutions: | |
|---|---|
| Concentrations | Volume for 100 ml |
| 20XSSC (3M NaCl .3 Trisodium citrate) | 50 |
| 100X Denhardts* | 20 |
| 1 M Sodium phosphate pH 6.5 | 10 |
| 10 mg/ml fish sperm DNA** | 20 |

*2% each Ficoll, bovine serum albumin, poly (vinyl pyrrolidone)
**treated to reduce fragment size to an average 1000 base pairs.

This solution is filtered through paper to remove small clumps. The volume is measured and an equal volume of deionized formamide is added. Lauryl sulfate (SDS) is then added to make a 1% solution.

| Final Concentrations | |
|---|---|
| SSC | 5X |
| Denhardts | 10X |
| Sodium phosphate pH 6.5 | .05 M |
| Fish sperm DNA | 1 mg/ml |
| Formamide | 50% |
| SDS | 1% |

This solution is heated to 95° C. and held at 95° C. to denature the fish sperm DNA. The solution is then rapidly cooled in an ice water bath to 72° C., placed in an appropriate container, and the blots are added. The container is placed in a 42° C. shaking incubator and gently agitated for at least 8 hours.

The hybridization solution is identical to the pre-hybridization solution except for the addition of the probe. $^{32}P$ labelled Tsex sequence, at a concentration of 0.05 μg/ml, is used as a probe. The hybridization solution is heated to 95° C. and held at 95° C. for 5–10 minutes to denature both the fish sperm DNA and the probe DNA. The hybridization solution is then rapidly cooled to 42° C., placed in a container, and the pre-hybridized Southern blots are added. The container is incubated at 42° C. with gentle agitation for 36 hours. Blots usually require 1 ml hybridization solution per 10 cm² surface area. Usually no more than 3–4 blots are placed in the same container. Since the hybridization solution dilutes the probe, additional labelled probe must be made if more than three blots (13×15 cm) are to be hybridized.

The blots are then washed three times for 10 minutes each in 2×SSC, 0.5% SDS, at room temperature, then washed 4 times for 30 minutes each in 2×SSC and blotted dry. The damp blots are wrapped in saran wrap and placed on X-ray film between two intensifying screens. Two to four days of exposure is required to visualize hybridization bands from a single copy genes, such as Tsex. After exposure, the X-ray film is developed by the standard procedure.

Summary of Hybridization Results

The Tsex sequence was labeled and used as a hybridization probe, employing the above described protocols, for hybridization against chromosomal DNA preparations from numerous bird species. Table 2 provides a summary of the hybridization patterns observed for DNA samples from male and female members of the species tested. Hybridization bands are assigned to either the W chromosome, the Z chromosome, or both sex chromosomes. Blank spaces in table 2 indicate the failure to test the indicated restriction endonuclease.

TABLE 2

Hybridization Patterns
(Bands in Kb)
Bird Chromosome

| BamHI | EcoRI | HindIII | SacI | TaqI | Pvu II |
|---|---|---|---|---|---|
| Turkey W | | | | | |
| 13.5 | 9.1 | 5.7 | 5.8 | 4.2 | 3.9 |
| 7.3 | 2.3 | 5.3 | | | |
| 6.4 | | 4.4 | | | |
| 5.5 | | | | | |
| Turkey Z | | | | | |
| 19.5 | 13.5 | 6.5 | 6.3 | 5.5 | 5.4 |
| | | | 3.4 | 1.9 | 2.6 |
| Turkey - nonspecific | | | | | |
| 11.5 | 3.9 | 2.5 | 6.7 | none | 7.7 |
| | 3.4 | | | | |
| Chicken W | | | | | |
| 9.7 | | 4.6 | | | |
| 4.8 | | 4.1 | | | |
| 1.65 | | | | | |
| 1.4 | | | | | |
| Chicken Z | | | | | |
| 6.1 | | | 8.2 | | |
| | | | 1.7 | | |
| Chicken-nonspecific | | | | | |
| none | | | 3.36 | | |
| Pheasant W | | | | | |
| | | | 8.5 | | |
| | | | 7.6 | | |
| | | | 6.6 | | |
| Pheasant Z | | | | | |
| | | | 5.1 | | |
| | | | 3.6 | | |
| | | | 2.95 | | |
| Canada W Geese | | | | | |
| 13 | | | | | |
| 7.7 | | | | | |
| Canada Geese Z | | | | | |
| 21 | | | | | |
| 14.5 | | | | | |
| Orange Wing Amazons W | | | | | |
| 7.1 | | 15.2 | | | |
| Orange Wing Amazons Z | | | | | |
| 14.3 | | 4.8 | | | |
| 8.6 | | | | | |
| Cockatiel W | | | | | |
| 12.6 | | 7.1 | | | |
| Cockatiel Z | | | | | |
| 20.1 | | 8.1 | | | |
| Conures Band Z | | | | | |
| | | 4.6 | | 1.7 | |
| Lovebirds | | | | | |

TABLE 2-continued

Hybridization Patterns
(Bands in Kb)
Bird Chromosome

| BamHI | EcoRI | HindIII | SacI | TaqI | Pvu II |
|---|---|---|---|---|---|
| Z Band | | | | | |
| | 8.1 | 7.3 | 6.4 | 2.2 | |
| | | | | 1.85 | |
| African Gray Parrot Z Band | | | | | |
| | 5.0 | 5.4 | 1.75 | 3.9 | |
| | | | | 3.2 | |
| Yellow Collar Macaws Z | | | | | |
| | | | | | 7.75 |
| Yellow Collar Macaws W | | | | | |
| | | | | | 5.9 |
| Blue & Gold Macaws Z | | | | | |
| | | | | | 6.3 |
| Blue & Gold Macaws W | | | | | |
| | | | | | 4.8 |
| Hyacinth Macaw Z | | | | | |
| | | | | | 7.7 |
| Hyacinth Macaw W | | | | | |
| | | | | | 6.3 |
| Scarlet Macaw Z | | | | | |
| | | | | | 7.3 |
| Scarlet Macaw W | | | | | |
| | | | | | 5.7 |

It is evident from the above results that a simple, accurate and efficient method is provided for determining the sex of birds at a stage when visual manifestations of sex characteristics are not apparent. In this manner, matings may be accurately made and other events associated with the sex of the bird may be properly performed.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A nucleic acid consisting of the sequence:

AACAGCATCT GATGCTGCAC CCCTTCAGTA

TCTGGCTCCC TACTCAGGCT GCTCCATGGG

GGAATACTTC AGAGACAATG GGAAACATGC

-continued

ATTGATCATC TACGATGACT TGTCCAAACA

GGCTGTTGCC TACCGTCAGA TGTCTCTGCT

GCTGCGTCGT CCGCCTGGCC GTGAAGCTTA

CCCAGGTGAT GTGTTCTACC TGCACTCTCG

CCTGCTGGAG AGAGCAGCTA AAATGAATGA

TTCCTTTGGA GGAGGCTCTC TGACTGCTTT

GCCCGTCATT GAAACTCAGG CTGGTGATGT

GTCTGCTTAC ATTCCAACCA ATGTCATCTC

CATCACTGAT GGACAGATCT TCTTGGAAAC

TGAACTGTTC TACAAAGGTA TCCGTCCAGC

CATCAACGTT GGTCTGTCTG TGTCCCGTGT

GGGTTCTGCT GCTCAGACCA GGGCAATGAA

ACAGGTGGCT GGTACCATGA AGCTGGAGCT

GGCTCAGTAC CGTGAAGTGG CTGCCTTTGC

TCAGTTTGGG TCTGATTTGG ATGCTGCCAC

ACAACAGCTG CTGAATCGTG GTGTGCGTCT

GACAGAGCTC CTGAAACAAG GACAGTATGT

TCCCATGGCT ATTGAGGAAC AGGTTGCAGT

CATCTATCGT GGTGTAAGAG GTCACTTGGA

CAAGCTGGAG CCCAGCAAAA TCACTAAATT

TGAGAGTGCT TTCCTGGCTC ATGTACTGAG

CCAGGACCAG GCCCTCCCTC TCCACCATCA

GGACTGAAGG GAAGATCTCT GACCAGACGG

AAGCTAAGCT GAAGGAAATA GTCACAAATT

TCCTATCTAC TTTTGAGGCA TAAACTCATT

ATCTGTTCAA ACAGACCAGG CTGTTTTTGT

TGTTACGTGC TTTGCCTCCA TCAAAGACCT

AAACGTATCG AGTGCTTGAA TGTACAGATC

TCACTGAGAA TAAAAGTTTC CATGTAAAA or the complementary sequence thereof or a fragment of at least fifty nucleotides thereof.

2. A hybridization probe comprising a fragment of at least fifty contiguous nucleotides of the sequence of claim 1 or said fragment joined to a label.

3. A hybridization probe according to claim 2, wherein said probe is joined to biotin, an enzyme, a fluorescer or a chemiluminescer.

4. A replication vector comprising at least fifty 14 contiguous nucleotides of the sequence of claim 1.

5. A method for determining whether an avian chromosomal DNA sample is from a genetically male or female bird;

wherein said bird is characterized by having a specific sequence on at least one of the sex W and Z chromosomes unique to the sex chromosome, said sequence being within the Tsex sequence in Table 1;

said method comprising:

preparing said avian chromosomal DNA sample for hybridizing or, when the distinction in sex is based on difference in restriction fragment length polymorphisms, a) digesting said avian chromosomal DNA sample with at least one restriction endonuclease; and b) size separating said restriction endonuclease digested DNA;

hybridizing said avian chromosomal DNA sample with a probe comprising a fragment of at least fourteen contiguous nucleotides of the sequence of claim 1 or said fragment joined to a label; and determining the presence, size and/or intensity of hybridizing bands as indicative of the sex of the bird.

6. A method according to claim 5, wherein said probe is the entire Tsex sequence.

7. A method according to claim 5, wherein said probe is labeled with a label capable of providing a detectable signal.

8. A method according to claim 5, wherein said bird is a turkey.

9. A method according to claim 5, wherein said bird is a chicken.

10. A method according to claim 5, wherein said sequence is both on the Z and W chromosomes and said determining is by size.

11. A method according to claim 5, wherein said sequence is on either the Z or W chromosome and said determining is by measuring the intensity of a labeled sized fragment.

12. A method according to claim 11, wherein said sized fragment is separated by gel electrophoresis.

13. A kit for the determination of the sex of a bird, comprising sample DNA from a bird of interest of known sex and a probe of claim 2.

14. A kit according to claim 13, wherein said sample DNA is chromosomal DNA.

* * * * *